United States Patent [19]

Bunce et al.

[11] Patent Number: 4,983,621

[45] Date of Patent: Jan. 8, 1991

[54] MEDICAMENTS

[75] Inventors: Keith T. Bunce, Luton; Patrick P. A. Humphrey, Bedford, both of England

[73] Assignee: Glaxo Group Limited, London, England

[21] Appl. No.: 375,913

[22] Filed: Jul. 6, 1989

[30] Foreign Application Priority Data

Jul. 7, 1988 [GB] United Kingdom ............... 8816187

[51] Int. Cl.$^5$ .......................................... A61K 31/415
[52] U.S. Cl. ..................................... 514/397; 424/10
[58] Field of Search ....................................... 514/397

[56] References Cited

U.S. PATENT DOCUMENTS

| | | | |
|---|---|---|---|
| 4,721,720 | 1/1988 | Wootton et al. | 514/304 |
| 4,753,789 | 6/1988 | Tyers et al. | 424/10 |
| 4,783,478 | 11/1988 | Wootton et al. | 514/397 |
| 4,851,407 | 7/1989 | Wootton et al. | 514/213 |

FOREIGN PATENT DOCUMENTS

| | | |
|---|---|---|
| 11490 | 5/1980 | European Pat. Off. . |
| 11489 | 12/1982 | European Pat. Off. . |
| 201165 | 11/1986 | European Pat. Off. . |
| 226266 | 6/1987 | European Pat. Off. . |
| 0272876 | 6/1988 | European Pat. Off. . |
| 2105193 | 3/1983 | United Kingdom . |

OTHER PUBLICATIONS

J. Clin. Oncology, 6, 4, Apr. 1988, 659–662 (Kris et al).
New Eng. J. of Med., Aug. 27, 1981, 529 (Aapro et al).
Int. J. Radiation Oncology Biol. Phys., 5, 1979, 2049–2052 (Stryker et al).
Radiation Research, 108, 1986, 307–316 (Carpenter et al).
ABPI Data Sheet Compendium 1986–1987, pp. 153–154.
Wein Med Wochenschr 1988, 138, 591–599 (Pfaffenrath et al).
Reserach Disclosure 294008 (Farmdoc Abstract 88-336052).

Primary Examiner—Stanley J. Friedman
Attorney, Agent, or Firm—Bacon & Thomas

[57] ABSTRACT

The invention relates to the co-administration in human or veterinary medicine of 1,2,3,9-tetrahydro-9-methyl-3-[(2-methyl-1H-imidazol-1-yl)methyl]-4H-carbazol-4-one or a physiologically acceptable salt or solvate thereof and a cyclo-oxygenase inhibitor such as indomethacin or piroxicam.

The two active ingredients, which may be administered separately either simultaneously or sequentially, or may be combined in a single pharmaceutical preparation, are useful in the relief and/or prevention of nausea and vomiting.

22 Claims, No Drawings

MEDICAMENTS

This invention relates to improvements in the treatment of gastrointestinal disorders. More particularly it relates to the use of a compound having antagonist activity at 5HT$_3$ receptors in conjunction with a cyclo-oxygenase inhibitor in the treatment of emesis, and to pharmaceutical compositions containing the two compounds.

In our UK Patent Specification No. 2153821A we disclose inter alia 1,2,3,9-tetrahydro-9-methyl-3-[(2-methyl-1H-imidazol-1-yl)methyl]-4H-carbazol-4-one which may be represented by the formula (I)

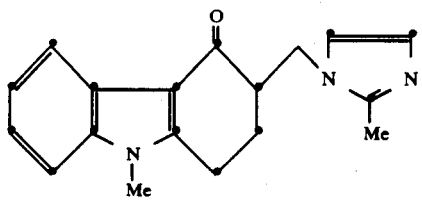

and physiologically acceptable salts, solvates and physiologically acceptable equivalents thereof.

In the aforementioned specification the compounds are described as potent and selective antagonists of 5-hydroxytryptamine (5HT) at 'neuronal' 5HT receptors of the type located on terminals of primary afferent nerves, and which are also present in the central nervous system. Receptors of this type are now designated 5HT$_3$ receptors. The compounds are described as being of use in the treatment of a human or animal subject suffereing from a condition caused by a disturbance of neuronal 5HT function, for example in the treatment of migraine pain or a psychotic disorder such as schizophrenia. The compounds may also be useful in the treatment of conditions such as anxiety, obesity and mania.

We have found, as described in our published European Patent Specification No. 226266, that the compounds disclosed in UK Patent Specification No. 2153821A additionally promote gastric emptying, and are thus useful in the treatment of conditions which may be relieved by the promotion of gastric emptying. Such conditions include gastric stasis and symptoms of gastrointestinal dysfunction such as dyspepsia, reflux oesophagitis, peptic ulcer and flatulence.

According to published European Patent Specification No. 226266, the compounds have also been found to be anti-emetics, and may be used in the treatment or prevention of nausea and vomiting. The use of these compounds for the treatment of emesis is also described in published European Patent Specification No. 201165, which specification additionally refers to the use of the compounds for the treatment of irritable bowel syndrome.

Tests in animals have shown that the anti-emetic properties of the compound of formula (I) may be significantly enhanced by administering the compound in conjunction with a cyclo-oxygenase inhibitor. Such co-administration is particularly useful in the treatment of emesis resulting from chemotherapy, especially cancer chemotherapy involving the use of, for example, cisplatin.

The present invention thus provides a method of treating and/or preventing nausea and vomiting, which comprises administering to a human or animal subject the compound of formula (I) or a physiologically acceptable salt or solvate thereof, and a cyclo-oxygenase inhibitor.

According to another aspect the invention provides for the use of the compound of formula (I) or a physiologically acceptable salt or solvate thereof for the manufacture of a medicament for administration in conjunction with a cyclo-oxygenase inhibitor, for the treatment and/or prevention of nausea and vomiting.

The compound of formula (I) or a physiologically acceptable salt or solvate thereof, and the cyclo-oxygenase inhibitor, may be administered as a single pharmaceutical composition comprising effective amounts of the two active ingredients. Alternatively the two active ingredients may be co-administered in the form of two separate pharmaceutical compositions for simultaneous or sequential use.

Suitable physiologically acceptable salts of the carbazolone of formula (I) for use according to the invention include acid addition salts formed with organic or inorganic acids, for example hydrochlorides, hydrobromides, sulphates, phosphates, citrates, fumarates and maleates. The solvates may, for example, be hydrates. A preferred form of the compound of formula (I) for use according to the invention is the hydrochloride, particularly in hydrated form, e.g. the dihydrate.

Suitable cyclo-oxygenase inhibitors that may be employed in the invention include systemic non-steroidal anti-inflammatory drugs such as, for example, aspirin, indomethacin, ibuprofen, piroxicam, fenoprofen, ketoprofen, naproxen, mefenamic acid, diflunisal, benorylate, azapropazone, diclofenac, fenbufen, feprazone, fenclofenac, flufenamic acid, flurbiprofen, oxyphenbutazone, phenylbutazone, sulindac and tolmetin.

Indomethacin and, more particularly, piroxicam represent preferred cyclo-oxygenase inhibitors for use according to the invention.

The dose at which the carbazolone of formula (I) and the cyclo-oxygenase inhibitor may be administered to man (of approximately 70 kg body weight) will depend upon the route of administration, the body weight of the patient, and the condition being treated and its severity.

A proposed dosage of the compound of formula (I) for use according to the invention is 0.05 to 25 mg, more preferably 0.05 to 20 mg, and most preferably 0.1 to 10 mg per unit dose, expressed as the weight of free base. The unit dose may be administered, for example, 1 to 4 times per day.

The cyclo-oxygenase inhibitor may conveniently be administered at doses within the normal dosage range at which the compound is therapeutically effective, for example 200 mg to 800 mg of mefenamic acid, 50 mg-1 g of aspirin, 10-100 mg of indomethacin and 5-50 mg of piroxicam per dosage unit taken one or more times daily in accordance with the normal dosage regime for the drug in question.

When the two active ingredients are administered as separate preparations, they may for example be given orally, parenterally (e.g. intramuscularly or, more particularly, intravenously) or rectally (e.g. by suppository), the cyclo-oxygenase inhibitor preferably being administered by the oral route.

The ability of cyclo-oxygenase inhibitors to enhance the anti-emetic properties of the carbazolone of formula (I) has been demonstrated in ferrets dosed with cisplatin, administering the drugs intraperitoneally, and observing the number of emetic episodes (vomits/retches) and/or the time during which emesis was inhibited.

According to a further aspect the invention provides a pharmaceutical composition, for use in human or veterinary medicine, comprising the compound of formula (I) or a physiologically acceptable salt or solvate thereof, and a cyclo-oxygenase inhibitor.

Compositions according to the invention may be formulated in conventional manner using one or more physiologically acceptable carriers or excipients. Thus the compositions may, for example, be formulated for oral, buccal, parenteral or rectal administration. Compositions for rectal administration or, more particularly, for administration by the oral route (e.g. as tablets or capsules) are preferred.

Compositions for oral use such as tablets and capsules may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of one or both active ingredients.

For parenteral administration the compositions may be presented in a form suitable for bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredients may be in powder form for constitution with a suitable vehicle, e.g. sterile pyrogen-free water, before use.

For rectal administration the compositions may be formulated as suppositories or retention enemas, e.g. containing conventional suppository bases such as cocoa butter or other glycerides.

The pharmaceutical compositions of the invention may be prepared according to conventional techniques well known in the pharmaceutical industry. Thus, for example, the compound of formula (I) or a salt or solvate thereof and the cyclo-oxygenase inhibitor may be admixed together, if desired, with suitable excipients. Tablets may be prepared, for example, by direct compression of such a mixture. Capsules may be prepared by filling the blend along with suitable excipients into gelatin capsules, using a suitable filling machine. Controlled release forms for oral or rectal administration may be formulated in a conventional manner associated with controlled release forms.

The compositions for use according to the invention may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration. Where the compound of formula (I) and the cyclo-oxygenase inhibitor are intended for administration as two separate compositions these may be presented in the form of, for example, a twin pack.

The following examples illustrate the preparation of the compound of formula (I). Temperatures are in °C.

EXAMPLE 1

1,2,3,9-Tetrahydro-9-methyl-3-[(2-methyl-1H-imidazol-1-yl)methyl]-4H-carbazol-4-one A solution of 3-[(dimethylamino)methyl]-1,2,3,9-tetrahydro-9-methyl-4H-carbazol-4-one hydrochloride (1.7 g) in water (17 ml) was treated with 2-methylimidazole (1.4 g) and then heated under reflux for 20 h. The cooled mixture was filtered and the residue washed with water (3×15 ml) to give a product (1.7 g) m.p. 221°–221.5°. This material was recrystallised from methanol to give the title compound (1.4 g) m.p. 231°–232°.

EXAMPLE 2

1,2,3,9-Tetrahydro-9-methyl-3-[(2-methyl-1H-imidazol-1-yl)methyl]-4H-carbazol-4-one hydrochloride dihydrate 1,2,3,9-Tetrahydro-9-methyl-3-[(2-methyl-1H-imidazol-1-yl)methyl]-4H-carbazol-4-one (18.3 g) in a hot mixture of isopropanol (90 ml) and water (18.3 ml) was treated with concentrated hydrochloric acid (6.25 ml). The hot mixture was filtered and the filtrate diluted with isopropanol (90 ml) and stirred at room temperature for 17 h, cooled to 2° and the solid filtered off (21.6 g). A sample (6 g) was recrystallised from a mixture of water (6 ml) and isopropanol (10 ml) to give the title compound as a white crystalline solid (6 g) m.p. 178.5°–179.5°.

Analysis Found: C,59.45;H,6.45;N,11.5. $C_{18}H_{19}N_3O \cdot HCl \cdot 2H_2O$ requires C,59.1;H,6.6;N,11.5%.

Water assay Found: 10.23%; $C_{18}H_{19}N_3O \cdot HCl \cdot 2H_2O$ requires 9.85%.

The following examples illustrate pharmaceutical compositions according to the invention, containing 1,2,3,9-tetrahydro-9-methyl-3-[(2-methyl-1H-imidazol-1-yl)methyl]-4H-carbazol-4-one hydrochloride dihydrate (Compound A) and piroxicam or mefenamic acid as the active ingredients. Compositions containing other physiologically acceptable salts or the compound of formula (I) in the form of its free base, or solvates thereof, and/or another cyclo-oxygenase inhibitor, may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques.

| Direct Compression | mg/tablet |
| --- | --- |
| Compound A | 5.0* |
| Piroxicam | 20.0 |
| Anhydrous lactose NF | 67.4 |
| Microcrystalline cellulose NF | 25.73 |
| Pregelatinised starch NF | 6.25 |
| Magnesium stearate BP | 0.62 |
| Compression weight | 125 mg |

*Equivalent to 4.0 mg free base.

Compound A and the piroxicam are sieved through a suitable sieve and blended with the lactose, microcrystalline cellulose, pregelatinised starch and magnesium stearate. The resultant mix is compressed into tablets using a suitable tablet press fitted with 7.0 mm normal concave punches.

Tablets of other strengths and/or combination of doses may be prepared by appropriate alterations in the amounts of the active ingredients and the excipients and using punches to suit.

| Wet Granulation | mg/tablet |
| --- | --- |
| Compound A | 10.0* |
| Mefenamic Acid BP | 500.0 |
| Lactose BP | 206.0 |
| Microcrystalline Cellulose USNF | 40.0 |
| Pregelatinised Starch USNF | 40.0 |
| Magnesium stearate BP | 4.0 |
| Compression weight | 800 mg |

*Equivalent to 8.0 mg free base

Compound A and the mefenamic acid are sieved through a suitable sieve and blended with the lactose, microcrystalline cellulose and pregelatinised starch. The blend is granulated with Purified Water BP and the granules are dried. The granules are screened and blended with the magnesium stearate. The granules are compressed into tablets using suitable punches.

Tablets of other strengths and/or combination of doses may be prepared by appropriate alterations in the amounts of the active ingredients and the excipients and using punches to suit.

| CAPSULES | mg/capsule |
| --- | --- |
| Compound A | 10.00* |
| Piroxicam | 20.0 |
| Pregelatinised Starch USNF | 54.625 |
| Magnesium stearate BP | 0.375 |
| Fill weight | 85.00 |

*Equivalent to 8.0 mg free base.

Compound A and the piroxicam are sieved through a 250 μm sieve and blended with the pregelatinised starch and magnesium stearate. The resultant mix is filled into size 3 hard gelatin capsules using a suitable filling machine.

Capsules of other strengths and/or combination of doses may be prepared by appropriate alterations in the amounts of the active ingredients and the excipients, using appropriately sized capsules.

We claim:

1. A pharmaceutical composition for use in human or veterinary medicine for the treatment and/or prevention of nausea and vomiting comprising an effective amount of 1,2,3,9-tetrahydro-9-methyl-3-[(2-methyl-1H-imidazol-1-yl)methyl]-4H-carbazol-4-one or a physiologically acceptable salt or solvate thereof, and an effective amount of a cyclo-oxygenase inhibitor, selected from the group consisting of piroxicam, mefenamic acid, and flufenamic acid.

2. A pharmaceutical composition according to claim 1 wherein said 1,2,3,9-tetrahydro-9-methyl-3-[(2-methyl-1H-imidazol-1-yl)methyl]-4H-carbazol-4-one is used in the form of a hydrochloride salt.

3. A pharmaceutical composition according to claim 2 wherein the 1,2,3,9-tetrahydro-9-methyl-3-[(2-methyl-1H-imidazol-1-yl)methyl]-4H-carbazol-4-one is used in the form of a hydrochloride dihydrate.

4. A pharmaceutical composition according to claim 1 wherein said cyclo-oxygenase inhibitor is piroxicam.

5. A pharmaceutical composition according to claim 1 in unit dose form containing 0.05 to 25 mg per unit dose of 1,2,3,9-tetrahydro-9-methyl-3-[(2-methyl-1H-imidazol-1-yl)methyl]-4H-carbazol-4-one expressed as the weight of free base and 5 to 50 mg of piroxicam per unit dose.

6. A pharmaceutical composition according to claim 5 in which said unit dose of 1,2,3,9-tetrahydro-9-methyl-3-[(2-methyl-1H-imidazol-1-yl)methyl]-4H-carbazol-4-one is 0.1 to 10 mg.

7. A pharmaceutical composition according to claim 1 in a form adapted for oral, parenteral or rectal administration.

8. A pharmaceutical composition according to claim 7 for oral administration in the form of tablets.

9. A pharmaceutical composition according to claim 1 containing at least one physiologically acceptable carrier or excipient.

10. A method for the treatment and/or prevention of nausea and vomiting which comprises administering to a human or animal subject an effective amount of 1,2,3,9-tetrahydro-9-methyl-3-[(2-methyl-1H-imidazol-1-yl)methyl]-4H-carbazol-4-one or a physiologically acceptable salt or solvate thereof in conjunction with an effective amount of a cyclo-oxygenase inhibitor selected from the group consisting of piroxicam, mefenamic acid and flufenamic acid.

11. A method according to claim 10 wherein said 1,2,3,9-tetrahydro-9-methyl-3-[(2-methyl-1H-imidazol-1-yl)methyl]-4H-carbazol-4-one is used in the form of a hydrochloride salt.

12. A method according to claim 11 wherein said 1,2,3,9-tetrahydro-9-methyl-3-[(2-methyl-1H-imidazol-1-yl)methyl]-4H-carbazol-4-one is used in the form of the hydrochloride dihydrate.

13. A method according to claim 10 wherein said cyclo-oxygenase inhibitor is piroxicam.

14. A method according to claim 13 wherein said 1,2,3,9-tetrahydro-9-methyl-3-[(2-methyl-1H-imidazol-1-yl)methyl]-4H-carbazol-4-one is administered in unit dose form of 0.05 to 25 mg per unit dose expressed as the weight of free base, and said piroxicam is administered in unit dose form of 5 to 50 mg per unit dose.

15. A method according to claim 14 in which said unit dose of 1,2,3,9-tetrahydro-9-methyl-3-[(2-methyl-1H-imidazol-1-yl)methyl]-4H-carbazol-4-one is 0.1 to 10 mg.

16. A method according to claim 10 wherein said 1,2,3,9-tetrahydro-9-methyl-3-[(2-methyl-1H-imidazol-1-yl)methyl]-4H-carbazol-4-one and said cyclo-oxygenase inhibitor are administered in a single medicament in a form adapted for oral, parenteral or rectal administration.

17. A method according to claim 16 wherein said medicament is for oral administration in the form of tablets.

18. A method according to claim 10 wherein said 1,2,3,9-tetrahydro-9-methyl-3-[(2-methyl-1H-imidazol-1-yl)methyl]-4H-carbazol-4-one and said cyclo-oxygenase inhibitor are administered separately.

19. A method according to claim 18 wherein said 1,2,3,9-tetrahydro-9-methyl-3-[(2-methyl-1H-imidazol-1-yl)methyl]-4H-carbazol-4-one and said cyclo-oxygenase inhibitor are each administered in a form adapted for oral, parenteral, or rectal administration.

20. A method according to claim 19 wherein said cyclo-oxygenase inhibitor is in a form adapted for oral administration.

21. A twin pack of medicaments for the treatment and/or prevention of nausea and vomiting comprising separate unit dose forms of an effective amount of 1,2,3,9-tetrahydro-9-methyl-3-[(2-methyl-1H-imidazol-1-yl)methyl]-4H-carbazol-4-one or a physiologically acceptable salt or solvate thereof and an effective amount of a cyclo-oxygenase inhibitor selected from the group consisting of piroxicam, mefenamic acid and flufenamic acid in association for separate administration.

22. A twin pack according to claim 21 wherein said cyclo-oxygenase inhibitor is piroxicam.

* * * * *